(12) United States Patent
Lee et al.

(10) Patent No.: US 9,522,873 B2
(45) Date of Patent: Dec. 20, 2016

(54) BIPHENYL DERIVATIVE, PHARMACEUTICALLY ACCEPTABLE SALT THEREOF, AND METHODS FOR PREVENTING OR TREATING INFLAMMATORY DISEASES OR AUTOIMMUNE DISEASES

(75) Inventors: Chang Hoon Lee, Gyeonggi-do (KR); Kyeong Lee, Gyeonggi-do (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 72 days.

(21) Appl. No.: 14/237,256

(22) PCT Filed: Aug. 6, 2012

(86) PCT No.: PCT/KR2012/006233
§ 371 (c)(1),
(2), (4) Date: Mar. 26, 2014

(87) PCT Pub. No.: WO2013/022243
PCT Pub. Date: Feb. 14, 2013

(65) Prior Publication Data
US 2015/0291509 A1    Oct. 15, 2015

(30) Foreign Application Priority Data
Aug. 5, 2011 (KR) .................. 10-2011-0078076

(51) Int. Cl.
| C07D 295/195 | (2006.01) |
| C07C 233/47 | (2006.01) |
| C07D 295/192 | (2006.01) |

(52) U.S. Cl.
CPC ......... *C07C 233/47* (2013.01); *C07D 295/192* (2013.01); *C07D 295/195* (2013.01)

(58) Field of Classification Search
CPC .............. C07D 295/023; C07D 265/30; C07D 295/027; C07C 213/02; C07C 213/74
USPC ................ 544/106, 391; 514/237.5; 562/492
See application file for complete search history.

(56) References Cited

U.S. PATENT DOCUMENTS

| 5,369,110 A | 11/1994 | Schmidlin et al. |
| 5,399,578 A | 3/1995 | Buhlmayer et al. |
| 2005/0085667 A1 | 4/2005 | Wood et al. |
| 2008/0132574 A1 | 6/2008 | Nakade et al. |

FOREIGN PATENT DOCUMENTS

| EP | 1745800 A1 * | 1/2007 |
| WO | 2005-009539 A2 | 2/2005 |
| WO | 2006-018325 A1 | 2/2006 |
| WO | 2006-083477 A2 | 8/2006 |

OTHER PUBLICATIONS

De Young et al., "Edema and Cell Infiltration in the Phorbol Ester-Treated Mouse Ear Are Temporally Separate and Can Be Differentially Modulated by Pharmacologic Agents", 26:335-341 (1989).
Gallo et al, "Biology and Clinical Relevance of Naturally Occurring Antimicrobial Peptides", Journal Allergy. Clinical Immunology, 110:823-831 (Dec. 2002).
Ryan et al, "Acute Inflammation", American Journal of Pathology, 86(1):185-276 (1977).
Hawiger, "Innate Immunity and Inflammation: a Transcriptional Paradigm", Immunology Research, 23(2-3):99-109 (2001).
Ho, "Aspirin-Triggered Lipoxin and Resolvin E1 Modulate Vascular Smooth Muscle Phenotype and Correlate With Peripheral Atherosclerosis", The American Journal of Pathology, 177(4), 2116-2123 (Oct. 2010).
Kupczyk, "Lipoxin A4 Generation Is Decreased in Aspirin-Sensitive Patients in Lysine-Aspirin Nasal Challenge in Vivo Model, Allergy", 64: 1746-1752 (2009).
Maderna et al., "Themed Section: Mediators and Receptors in the Resolution of Inflammation: Lipoxins: Resolutionary Road", British Journal of Pharmacology, 158:947-959 (2009).
Nathan, "Nonresolving Inflammation", Cell 140, 871-882 (Mar. 19, 2010).
Spite, "Resolvin D2 Is a Potent Regulator of Leukocytes and Controls Microbial Sepsis", Nature, 461(7268) 1287-1291 (Oct. 29, 2009).
Ku, "Resolvins RvE1 and RvD1 Attenuate Inflammatory Pain via Central and Peripheral Actions", National Medicine, 16(5), 592-597 (May 2010).

* cited by examiner

*Primary Examiner* — Alicia L Otton
*Assistant Examiner* — Sagar Patel
(74) *Attorney, Agent, or Firm* — Dardi & Herbert, PLLC; Curtis Herbert

(57) ABSTRACT

The present invention relates to a novel biphenyl derivative or a pharmaceutically acceptable salt thereof, a pharmaceutical composition for preventing or treating inflammatory diseases or autoimmune diseases comprising the same as an active ingredient, and methods for treating inflammatory disease or autoimmune diseases with the pharmaceutical composition. Novel biphenyl derivatives according to the present invention promote the phagocytosis of macrophages and inhibit the chemotaxis to exhibit excellent inflammation terminating and anti-inflammatory effects and thus can be effectively used as therapeutic agents for inflammatory diseases or autoimmune diseases.

4 Claims, 8 Drawing Sheets

Vehicle

TPA

0.3% compound 6

1% compound 6

0.5% Indo

Vehicle

TPA 0.3% compound 6

1% compound 6

0.5% Indo

BIPHENYL DERIVATIVE, PHARMACEUTICALLY ACCEPTABLE SALT THEREOF, AND METHODS FOR PREVENTING OR TREATING INFLAMMATORY DISEASES OR AUTOIMMUNE DISEASES

CROSS REFERENCE TO RELATED APPLICATIONS

This application is a national stage filing of PCT Application PCT/KR2012/006233 filed Aug. 6, 2012, which claims prior to Korean Patent Application No. 10-20110078076 filed Aug. 5, 2011, all of which applications are hereby incorporated by reference herein.

TECHNICAL FIELD

The present invention relates to a novel biphenyl derivative or a pharmaceutically acceptable salt thereof, and a pharmaceutical composition for preventing or treating inflammatory diseases or autoimmune diseases comprising the same as an active ingredient.

BACKGROUND OF THE INVENTION

The inflammatory response is a defense mechanism caused by various factors such as infection with pathogens or tissue injury and takes initial protective action to limit damage to an infected or injured area. In most cases, the inflammatory response leads to the removal of pathogenic factors and the induction of specific adaptive immunity by the components of innate immunity (Hawiger J., 2001). Redness, swelling, heat, pain, etc., known to be accompanied by inflammation, are the results of continuous inflammatory responses such as increased local blood flow and decreased local blood flow rate due to vasodilation caused by the action of inflammatory mediators and cytokines in the inflammation site, increased extravasation of plasma components due to increased permeability of blood vessels, increased extravasation of immune cells due to increased adhesion of vascular endothelial cells to circulating immune cells, and increased migration to the infected area by chemotaxis (Gallo R L, Murakami M, Takaaki O, Zaiou M., 2002; Graeme B. Ryan, M B, and Guido M., 1977).

Inflammation occurs in two phases. In the first phase, prostaglandins, leukotrienes (LT), etc. play an important role in the inflammatory response. That is, they induce strong chemotactic responses in leukocytes, which are also associated with the production of cytokines induced by Th1 (Maderna & Godson 2009). In the second phase, the production of lipid mediators, which actively control inflammation and promote the termination of inflammation, i.e., the resolution of inflammation, has recently been found.

INTRODUCTION AND SUMMARY OF THE INVENTION

In addition to the existing theory that acute inflammation terminates itself when the cause is resolved, but chronic inflammation persists until the cause is removed, a new theory that chronic inflammatory disease occurs due to abnormal termination of inflammation has been proposed.

It was reported that the diseases caused by the abnormal termination of inflammation include asthma, irritable colitis, rheumatoid arthritis, multiple sclerosis, atherosclerosis, chronic obstructive pulmonary disease, etc. (Nathan, 2010).

Moreover, it is known that if fragments of apoptotic neutrophils, which play an important role in the termination of inflammation, are not properly cleared by macrophages, antibodies against various proteins isolated from the fragments of neutrophils are formed, leading to autoimmune diseases. That is, the abnormal termination of inflammation is one of the important factors that cause autoimmune diseases.

While it has been known that the termination of inflammation is a phenomenon that occurs naturally and passively when the levels of substances that trigger inflammation are reduced, Serhan etc. have discovered lipoxins, resolvins, protectins, etc. and found that the termination of inflammation is actively promoted, like prostaglandins involved in the triggering of inflammation. It has been reported that compounds that actively promote the termination of inflammation are effective in various chronic inflammatory diseases. For example, it has been reported that Resolvin E1 is effective in pain and Resolvin D2 is inhibits sepsis (Xu, 2010, Spite, 2009). Moreover, Haworth, etc. have reported that RvE1 induces the termination of inflammation to exhibit effects on allergic inflammatory diseases. Furthermore, it has been reported that the levels of factors that actively promote the termination of inflammation in chronic inflammatory diseases, i.e., the levels of lipoxin A4 and lipoxins induced by aspirin are observed low in asthmatic patients and atherosclerotic patients (Kupczyk, 2009; Ho, 2010).

Therefore, various attempts to treat diseases associated with the abnormal termination of inflammation with new substances that induce the termination of inflammation have been made, but the compounds known to belong to lipoxins, resolvins, etc. are metabolically unstable due to several double bonds present in their structures and thus rapidly degraded in vivo. Therefore, it is somewhat difficult to mass-produce these substances for the development of drugs, leading to a significant problem of druggability.

Accordingly, in order to solve the above conventional problems, the present inventors have made many efforts to develop a substance that induces more effective termination of inflammation, synthesized a novel biphenyl derivative, found that the biphenyl derivative induces the termination of inflammation and has therapeutic effects on inflammatory diseases or autoimmune diseases, thus completing the present invention.

An object of the present invention is to provide a novel biphenyl derivative or a pharmaceutically acceptable salt thereof, and a preparation method thereof.

Another object of the present invention is to provide a pharmaceutical composition for preventing or treating inflammatory diseases or autoimmune diseases, comprising the novel biphenyl derivative or a pharmaceutically acceptable salt thereof as an active ingredient.

To accomplish the above objects, the present invention provides provide a novel biphenyl derivative or a pharmaceutically acceptable salt thereof, and a preparation method thereof.

Moreover, the present invention provides a pharmaceutical composition for preventing or treating inflammatory diseases or autoimmune diseases, comprising the novel biphenyl derivative or a pharmaceutically acceptable salt thereof as an active ingredient.

The novel biphenyl derivatives or pharmaceutically acceptable salts thereof according to the present invention promote the phagocytosis of macrophages and inhibit the chemotaxis to exhibit excellent inflammation terminating and anti-inflammatory effects and thus can be effectively used as therapeutic agents for inflammatory diseases or autoimmune diseases.

DETAILED DESCRIPTION AND EXAMPLES

Figure 1:
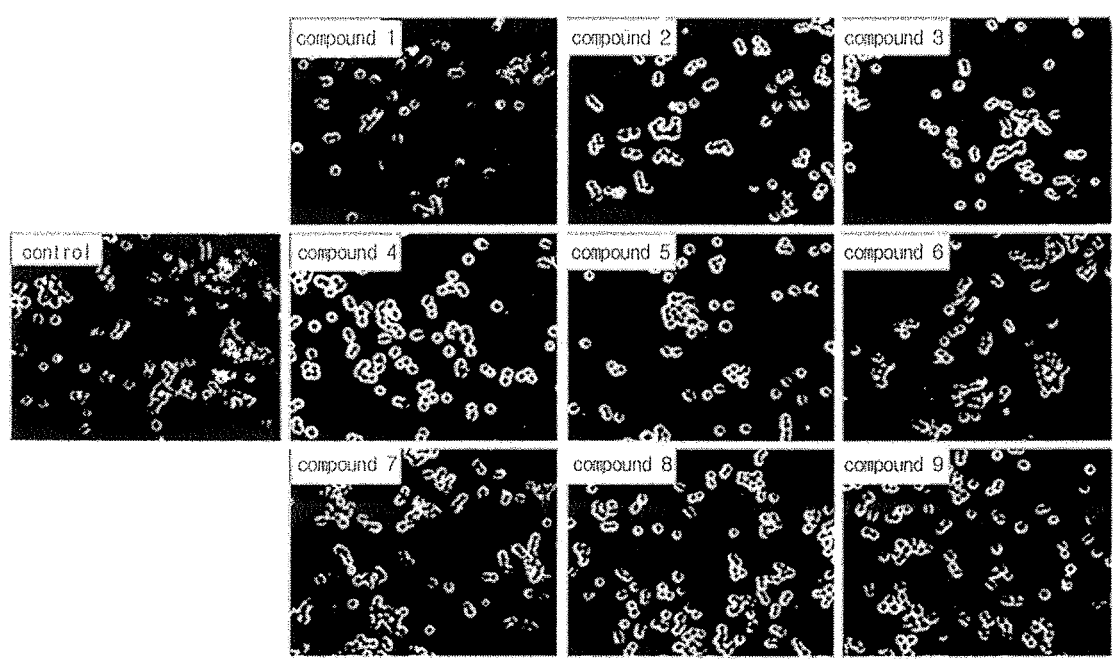
FIG. 1 is a montage of photomicrographs showing the promotion of phagocytosis of macrophages by biphenyl derivatives of the present invention.

Hereinafter, the present invention will be described in detail.

The present invention provides a biphenyl derivative or a pharmaceutically acceptable salt thereof represented by the following formula 1:

[Formula 1]

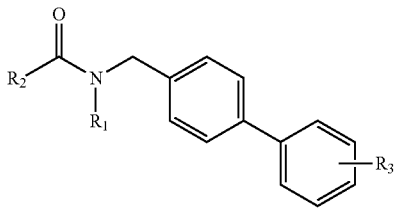

wherein $R_1$ is phenyl or halogen-substituted phenyl,
$R_2$ is $C_1$-$C_{10}$ alkyl, and
$R_3$ is $C_5$-$C_{20}$ heteroaryl or —(C=O)-A, wherein A is OH or $C_1$-$C_4$ alkyl-substituted or unsubstituted $C_5$-$C_{20}$ heteroaryl.

Preferably, in formula 1, $R_1$ is phenyl or 3-fluorophenyl, $R_2$ is butyl or pentyl, and
$R_3$ is —(C=O)-A, wherein A is OH, 4-methylpiperazinyl or morpholinyl.

The compound of formula 1 of the present invention may be selected from the group consisting of the following compounds:
1) 4'-[(N-phenylpentanamido)methyl]biphenyl-2-carboxylic acid);
2) 4'-[(N-phenylpentanamido)methyl]biphenyl-3-carboxylic acid;
3) 4'-[(N-phenylpentanamido)methyl]biphenyl-4-carboxylic acid;
4) N-[(2'-(4-methylpiperazine-1-carbonyl)biphenyl-4-yl)methyl]-N-phenylpentanamide;
5) N-[(3'-(4-methylpiperazine-1-carbonyl)biphenyl-4-yl)methyl]-N-phenylpentanamide;
6) N-[(4'-(4-methylpiperazine-1-carbonyl)biphenyl-4-yl)methyl]-N-phenylpentanamide;
7) 4'-[(N-(3-fluorophenyl)pentanamido)methyl]biphenyl-2-carboxylic acid;
8) 4'-[(N-(3-fluorophenyl)pentanamido)methyl]biphenyl-3-carboxylic acid;
9) 4'-[(N-(3-fluorophenyl)pentanamido)methyl]biphenyl-4-carboxylic acid;
10) 4'-[(N-(3-fluorophenyl)hexanamido)methyl]biphenyl-4-carboxylic acid;
11) N-(3-fluorophenyl)-N-[(4'-(morpholine-4-carbonyl)biphenyl-4-yl)methyl]pentanamide; and
12) N-(3-fluorophenyl)-N-[(4'-(4-methylpiperazine-1-carbonyl)biphenyl-4-yl)methyl]hexanamide.

The biphenyl derivative of formula 1 of the present invention may be used in the form of a pharmaceutically acceptable salt and may include salts, hydrate, and solvates prepared according to conventional methods. Preferably, suitable salts include acid addition salts formed with various pharmaceutically or physiologically acceptable free acids. Such free acids include organic acids and inorganic acids. Examples of the inorganic acids may include, but not limited to, hydrochloric acid, bromic acid, sulfuric acid, phosphoric acid, etc., and examples of the organic acids may include, but not limited to, citric acid, acetic acid, lactic acid, tartaric acid, fumaric acid, formic acid, propionic acid, oxalic acid, trifluoroacetic acid, methanesulfonic acid, benzenesulfonic acid, maleic acid, benzoic acid, gluconic acid, glycolic acid, succinic acid, 4-morpholineethanesulfonic acid, camphorsulfonic acid, 4-nitrobenzenesulfonic acid, hydroxy-O-sulfonic acid, 4-toluenesulfonic acid, knife ruktu acid, EMBO acid, glutamic acid, aspartic acid, etc. Moreover, pharmaceutically acceptable metal salts may be prepared using bases. For example, alkali metal or alkali earth metal salts may be obtained by dissolving the compound in an excess of an alkali metal hydroxide or alkali earth metal hydroxide solution, filtering non-dissolved compound salts, and evaporating and drying the filtrate. Here, sodium, potassium, or calcium salts are pharmaceutically suitable metal salts, but not limited thereto. Furthermore, silver salts corresponding to the metal salts may be obtained by reacting alkaline metals or alkali earth metals with suitable silver salts (e.g. nitrate).

Moreover, the present invention provides a method for preparing a biphenyl derivative or a pharmaceutically acceptable salt thereof represented by formula 1.

The method for preparing a biphenyl derivative or a pharmaceutically acceptable salt thereof represented by formula 1 may comprise the steps of:

(1) preparing a compound of formula 2 by reacting bromobenzoic acid with thionyl chloride ($SOCl_2$) in the presence of an organic solvent;

(2) preparing a compound of formula 3 by reacting the compound of formula 2 with 4-formylphenylboronic acid in the presence of an organic solvent;

(3) preparing a compound of formula 4 by reacting the compound of formula 3 with an amine compound in the presence of an organic solvent;

(4) preparing a compound of formula 5 by reacting the compound of formula 4 with an acyl chloride compound in the presence of an organic solvent; and (5) preparing a compound of formula 1 by reacting the compound of formula 5 with lithium hydroxide monohydrate in the presence of an organic solvent.

Moreover, the method for preparing a biphenyl derivative or a pharmaceutically acceptable salt thereof represented by formula 1 may further comprise, after step (5), the step of (6) substituting a carboxylic acid group of the compound of formula 1 for a heteroaryl group by reacting the compound of formula 1 with a heteroaryl compound in the presence of an organic solvent.

The organic solvent used in each step may include methanol, dichloromethane, acetonitrile, tetrahydrofuran, 1,4-dioxane, dimethylamide, etc., but not limited thereto.

The amine compound used in step (3) may include aliphatic or aromatic amine compounds, preferably aniline or 3-fluoroaniline.

The acyl chloride compound used in step (4) may include valeryl chloride, caproyl chloride, etc., but not limited thereto.

In the compound of formula 1 of the present invention, when $R_1$ is phenyl, $R_2$ is butyl, and $R_3$ is COOH or 4-methylpiperazinyl, a representative preparation process is represented by the following reaction scheme 1:

[Reaction Scheme 1]

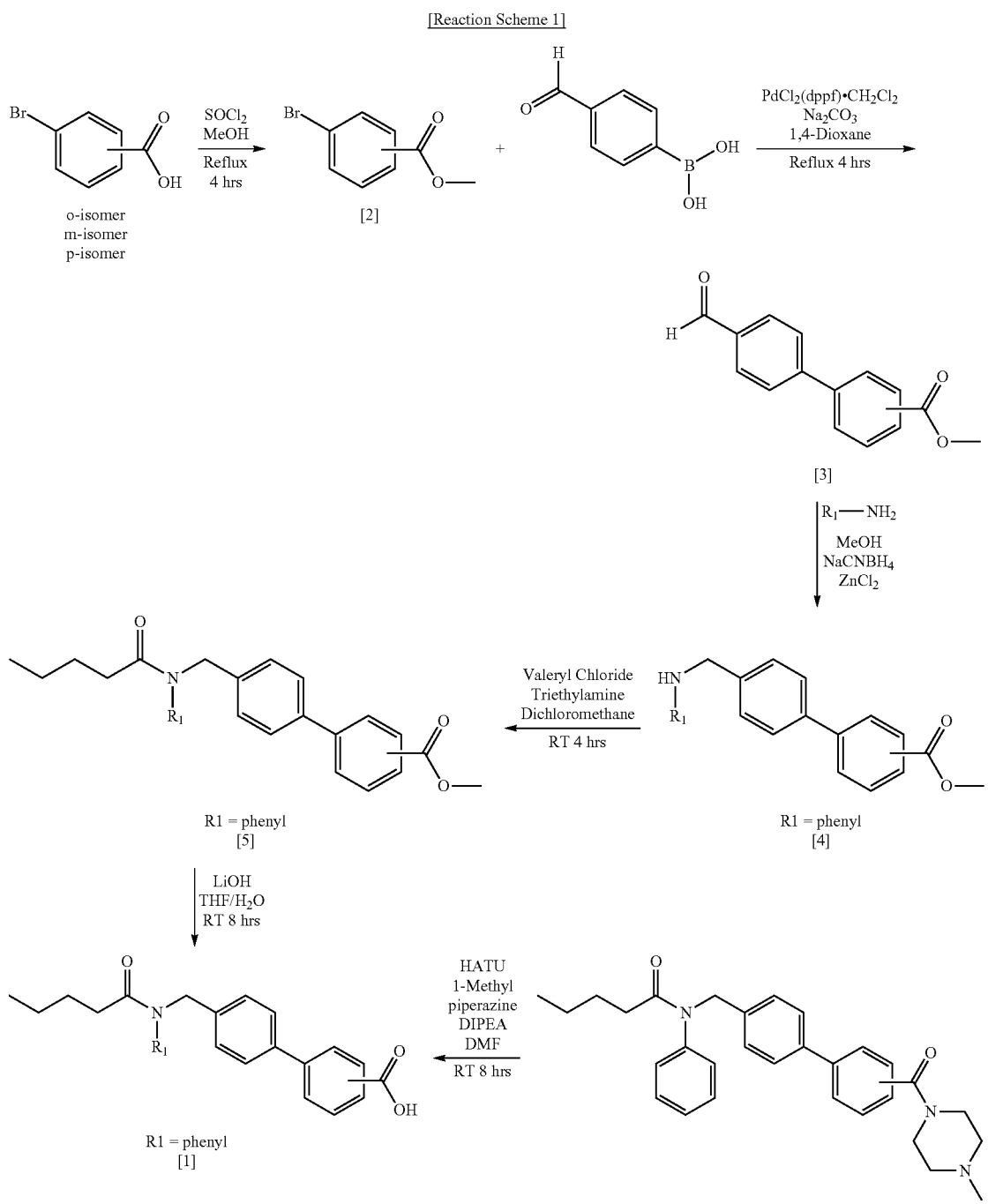

The reagent and solvents used in the above reaction scheme and the reaction order may be changed or modified, but not limited thereto. In particular, those skilled in the art can fully understand the biphenyl derivative represented by formula 1 of the present invention can be prepared by various methods well known in the art.

Moreover, the present invention provides a pharmaceutical composition for preventing or treating inflammatory diseases or autoimmune diseases, comprising the biphenyl derivative or a pharmaceutically acceptable salt thereof as an active ingredient.

The novel biphenyl derivatives according to the present invention promote the phagocytosis of macrophages and inhibit the chemotaxis to exhibit excellent inflammation terminating and anti-inflammatory effects and thus can be effectively used to prevent or treat inflammatory diseases or autoimmune diseases.

In the present invention, the inflammatory diseases or autoimmune diseases are caused by abnormal termination of inflammation, and in particular may include dermatitis, allergy, atopy, conjunctivitis, periodontitis, rhinitis, tympanitis, pharyngolaryngitis, tonsillitis, pneumonia, gastric ulcer, gastritis, Crohn's disease, colitis, irritable colitis, hemorrhoids, gout, ankylosing spondylitis, lupus, fibromyalgia, psoriasis, arthritis, osteoarthritis, rheumatoid arthritis, periarthritis of shoulder, tendinitis, tenosynovitis, peritendinitis, myositis, hepatitis, cystitis, nephritis, Sjogren's syndrome, multiple sclerosis, acute and chronic inflammatory diseases, erythema, Hashimoto's thyroiditis, pernicious anemia, Addison's disease, type 1 diabetes, chronic fatigue syndrome, hypothyroidism, hyperthyroidism, scleroderma, Behcet's disease, inflammatory bowel disease, myasthenia gravis, Meniere's syndrome, Guillain-Barre syndrome, leukoplakia, endometriosis, systemic sclerosis, atheriosclerosis, chronic obstructive pulmonary disease, and asthma, but not limited thereto.

The composition of the present invention may further comprise one or more known active ingredients having the effect of treating inflammatory diseases or autoimmune diseases in combination with the biphenyl derivative or a pharmaceutically acceptable salt thereof as an active ingredient.

The composition of the present invention may further comprise suitable carriers, excipients, and diluents that are conventionally used for the preparation of pharmaceutical compositions. The composition of the present invention may be used as oral formulations such as powders, granules, tablets, capsules, suspensions, emulsions, syrups, aerosols, etc., external formulations, suppositories, and sterile injections by general methods. Suitable formulations known in the art may preferably include those disclosed in the literature (Remington's Pharmaceutical Science, recent edition, Mack Publishing Company, Easton Pa.). Examples of carriers, excipients, and diluents, which may be included in the composition of the present invention, may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate, and mineral oil. Formulations may be prepared by using diluents or excipients such as fillers, extenders, binders, humectants, disintegrators, surfactants, etc. that are generally used. Solid formulations for oral administration may include tablets, pills, powders, granules, capsules, etc. and these solid formulations may be prepared by mixing one or more excipients such as starch, calcium carbonate, sucrose, lactose, gelatin, etc. with the composition. Moreover, lubricants such as magnesium stearate, talc, etc. may be used in addition to simple excipients. Liquid formulations for oral administration may include suspensions, liquid for internal use, emulsions, syrups, etc., and various excipients such as humectants, sweeteners, aromatics, preservatives, etc. may be included in addition to generally-used simple diluents such as water and liquid paraffin. Formulations for parenteral administration may include sterile solutions, non-aqueous solvents, suspensions, emulsions, freeze-dried formulations, and suppositories. Propylene glycol, polyethylene glycol, vegetable oil such as olive oil, and injectable ester such as ethylolate, etc. may be used for non-aqueous solvents and suspensions. Witepsol, macrogol, Tween 61, cacao oil, laurin oil, glycerogelatin, etc. may be used for suppository bases.

As used herein the term "administration" is intended to mean providing the composition of the present invention to a subject by any appropriate method.

The preferred dosage of the pharmaceutical composition of the present invention may vary depending on the condition and body weight of a patient, severity of disease, drug form, administration route, and administration period, but may be appropriately selected by those skilled in the art. For desired effects, the composition of the present invention may be administered in a dose of about 0.0001 to about 1,000 mg/kg body weight per day. The composition may be administered once a day or in equally divided doses.

The pharmaceutical composition of the present invention may be administered to a subject by various routes. All modes of administration may be contemplate, for example, orally, intrarectally, or injected intravenously, intramuscularly, subcutaneously, intrauterinely, or intracerebroventricularly.

For the prevention or treatment of inflammatory diseases or autoimmune diseases, the composition of the present invention may be used alone or in combination with surgical operation, radiotherapy, hormonal therapy, chemical therapy, and methods using biological response modifiers.

In the following, preferred Examples, Experimental Examples, and Preparation Examples will be provided for better understanding of the present invent. However, the following Examples, Experimental Examples, and Preparation Examples are provided only for illustration of the present invention, and the present invention is not limited by the Examples, Experimental Examples, and Preparation Examples.

Example 1

Preparation of Novel Biphenyl Derivatives 1-1. Preparation of methyl-2-bromobenzoate

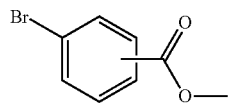

2-bromobenzoic acid (o-isomer) (3.25 g, 15.25 mmol) was added to methanol (50 ml) and cooled in ice, and then thionyl chloride (5.41 ml, 74.58 mmol) was slowly added for about 15 minutes. After removing the ice, the mixture was stirred at 90° C. for 4 hours. The mixture was cooled at room temperature, filtered, concentrated, and then purified by silica gel column chromatography (EtOAc:hexanes=1:9), yielding methyl-2-bromobenzoate as a colorless oil (5.08 g, 95% yield).

Moreover, methyl-3-bromobenzoate or methyl-4-bromobenzoate was obtained by the above method using isomer 3-bromobenzoic acid (m-isomer) or 4-bromobenzoic acid (p-isomer) which was different from 2-bromobenzoic acid.

The obtained compounds were characterized by $^1$H-NMR, and the results are as follows:

Methyl-2-bromobenzoate: $^1$H-NMR (DMSO-d$_6$, 500 MHz) δ 7.94 (1H, m, aromatic-H), 7.69 (1H, m, aromatic-H), 7.59 (1H, m, aromatic-H), 7.33 (1H, m, aromatic-H), 3.84 (3H, s, —OCH$_3$).

Methyl-3-bromobenzoate $^1$H-NMR (DMSO-d$_6$, 500 MHz) δ 8.05 (1H, s, aromatic-H), 7.91 (1H, m, aromatic-H), 7.59 (1H, m, aromatic-H), 7.33 (1H, m, aromatic-H), 3.84 (3H, s, —OCH$_3$).

Methyl-4-bromobenzoate: $^1$H-NMR (DMSO-d$_6$, 500 MHz) δ 7.76 (2H, d, aromatic-H), 7.69 (2H, d, aromatic-H), 3.84 (3H, s, —OCH$_3$).

1-2. Preparation of Methyl-4'-formylbiphenyl-2-carboxylate

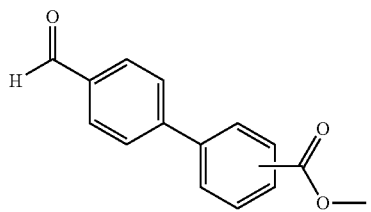

Methyl-2-bromobenzoate (2.0 g, 9.30 mmol) obtained in Example 1-1 and 4-formylphenylboronic acid (1.46 g, 9.76 mmol) were added to a stirring solution of 1,4-dioxane (20 mL) and water (4 mL). The mixture was degassed with argon for 15 minutes, and PdCl$_2$ (dppf)CH$_2$Cl$_2$ (0.379 g, 0.46 mmol) and Na$_2$CO$_3$ (2.38 g, 23.25 mmol) were added thereto. The mixture was degassed again and stirred at 95° C. for 4 hours. The mixture was cooled at room temperature, diluted with ethyl acetate, and filtered through a celite bed. The filtrate was washed with brine, and the organic solvent layer was collected, concentrated, and purified by silica gel column chromatography (n-Hexane:EtOAc=1:4), yielding methyl-4'-formylbiphenyl-2-carboxylate as a while solid phase (2.0 g, 90.0% yield).

Moreover, methyl-4'-formylbiphenyl-3-carboxylate or methyl-4'-formylbiphenyl-4-carboxylate were obtained by the above method using methyl-3-bromobenzoate or methyl-4-bromobenzoate prepared in Example 1-1 using isomers different from 2-bromobenzoic acid.

The obtained compounds were characterized by $^1$H-NMR, and the results are as follows:

Methyl-4'-formylbiphenyl-2-carboxylate: $^1$H-NMR (DMSO-d$_6$, 500 MHz) δ 10.06 (1H, s, aldehydic), 8.25 (1H, m, aromatic-H), 7.95 (2H, d, aromatic-H), 7.82 (2H, d, aromatic-H), 7.70 (1H, m, aromatic-H), 7.52 (1H, m, aromatic-H), 7.33 (1H, m, aromatic-H), 3.86 (3H, s, —OCH$_3$).

Methyl-4'-formylbiphenyl-3-carboxylate: $^1$H-NMR (DMSO-d$_6$, 500 MHz) δ 10.07 (1H, s, aldehydic), 8.27 (1H, m, aromatic-H), 8.05 (1H, d, aromatic-H), 8.04 (3H, m, aromatic-H), 796 (2H, d, aromatic-H), 7.68 (1H, m, aromatic-H), 3.90 (3H, s, —OCH$_3$).

Methyl-4'-formylbiphenyl-4-carboxylate: $^1$H-NMR (DMSO-d$_6$, 500 MHz) δ 10.08 (1H, s, aldehydic), 8.09 (2H, d, aromatic-H), 8.06 (2H, d, aromatic-H), 8.04 (2H, d, aromatic-H), 7.93 (2H, d, aromatic-H), 3.89 (3H, s, —OCH$_3$).

1-3. Preparation of methyl-4'-[(phenylamino)methyl]biphenyl-2-carboxylate

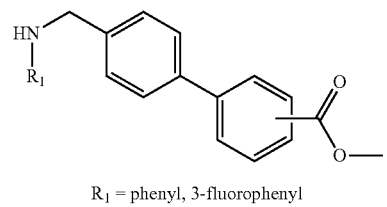

R$_1$ = phenyl, 3-fluorophenyl

A methanol solution (5 mL) in which sodium cyanoborohydride (4.0 ml (1M), 4.16 mmol) and zinc chloride (4.0 ml (0.5M), 2.08 mmol) were dissolved was slowly added at room temperature to a methanol solution (10 mL) in which methyl-4'-formylbiphenyl-2-carboxylate (1.0 g, 4.16 mmol) obtained in Example 1-2 and aniline (1.16 g, 12.48 mmol) were dissolved, and the mixture was stirred at room temperature for 4 hours. The mixture was concentrated under reduced pressure, diluted with ethyl acetate, and washed with brine and water. Then, the organic solvent layer was collected, dehydrated with anhydrous MgSO$_4$, and filtered, and then the resulting organic solvent layer was concentrated by evaporation. The concentrate was purified by silica gel column chromatography (n-Hexane:EtOAc=4:1), yielding methyl-4'-[(phenylamino)methyl]biphenyl-2-carboxylate as a white solid phase (1.13 g, 86% yield).

Moreover, methyl-4'-[(phenylamino)methyl]biphenyl-3-carboxylate or methyl-4'-[(phenylamino)methyl]biphenyl-4-carboxylate were obtained by the above method using methyl-4'-formylbiphenyl-3-carboxylate or methyl-4'-formylbiphenyl-4-carboxylate prepared in Example 1-2 using isomers different from methyl-4'-formylbiphenyl-2-carboxylate.

The obtained compounds were characterized by $^1$H-NMR, and the results are as follows:

Methyl-4'-[(phenylamino)methyl]biphenyl-2-carboxylate: $^1$H-NMR (DMSO-d$_6$, 500 MHz) δ 7.70 (1H, m, aromatic-H), 7.60 (1H, m, aromatic-H), 7.47 (1H, m, aromatic-H), 7.40 (3H, m, aromatic-H), 7.23 (2H, m, aromatic-H), 7.03 (2H, m, aromatic-H), 6.58 (2H, m, aromatic-H), 6.50 (1H, m, aromatic-H) 6.27 (1H, t, —NH 4.32 (2H, d, —CH$_2$), 3.88 (3H, s, —OCH$_3$).

Methyl-4'-[(phenylamino)methyl]biphenyl-3-carboxylate: $^1$H-NMR (DMSO-d$_6$, 500 MHz) δ 7.94 (1H, m, aromatic-H), 7.65 (2H, d, aromatic-H), 7.60 (1H, m, aromatic-H), 7.47 (2H, d, aromatic-H), 7.04 (2H, m, aromatic-H), 6.58 (3H, m, aromatic-H), 6.50 (2H, m, aromatic-H), 6.28 (1H, m, —NH), 4.32 (2H, d, —CH$_2$), 3.88 (3H, s, —OCH$_3$).

Methyl-4'-[(phenylamino)methyl]biphenyl-4-carboxylate: $^1$H-NMR (DMSO-d$_6$, 500 MHz) δ 8.01 (2H, d, aromatic-H), 7.81 (2H, d, aromatic-H), 7.70 (2H, d, aromatic-H), 7.48 (2H, d, aromatic-H), 7.03 (2H, m, aromatic-H), 6.58 (2H, d, aromatic-H), 6.50 (1H, m, aromatic-H), 6.28 (1H, t, —NH), 4.32 (2H, d, —CH$_2$), 3.86 (3H, s, —OCH$_3$).

Moreover, methyl-4'-[(3-fluorophenylamino)methyl]biphenyl-2-carboxlyate, methyl-4'-[(3-fluorophenylamino)methyl]biphenyl-3-carboxlyate, or methyl-4'-[(3-fluorophenylamino)methyl]biphenyl-4-carboxlyate was obtained using 3-fluoroaniline instead of aniline by the above method using methyl-4'-formylbiphenyl-2-carboxylate, methyl-4'-formylbiphenyl-3-carboxylate, or methyl-4'-formylbiphenyl-4-carboxylate obtained in Example 1-2.

The obtained compounds were characterized by $^1$H-NMR, and the results are as follows:

Methyl-4'-[(3-fluorophenylamino)methyl]biphenyl-2-carboxlyatel: $^1$H-NMR (DMSO-$d_6$, 500 MHz) δ 8.16 (1H, s, aromatic-H), 7.93 (2H, m, aromatic-H), 7.68 (2H, m, aromatic-H), 7.60 (1H, m, aromatic-H), 7.43 (2H, m, aromatic-H), 7.04 (1H, m, aromatic-H), 6.64 (1H, m, —NH), 6.43 (1H, m, aromatic-H), 6.32 (1H, m, aromatic-H), 6.25 (1H, m, aromatic-H), 4.32 (2H, d, —CH$_2$), 3.88 (3H, s, —OCH$_3$).

Methyl-4'-[(3-fluorophenylamino)methyl]biphenyl-3-carboxlyatel: $^1$H-NMR (DMSO-$d_6$, 500 MHz) δ 8.17 (1H, s, aromatic-H), 7.94 (2H, m, aromatic-H), 7.68 (2H, m, aromatic-H), 7.61 (1H, m, aromatic-H), 7.47 (2H, m, aromatic-H), 7.04 (1H, m, aromatic-H), 6.64 (1H, m, —NH), 6.43 (1H, m, aromatic-H), 6.32 (1H, m, aromatic-H), 6.25 (1H, m, aromatic-H), 4.32 (2H, d, —CH$_2$), 3.88 (3H, s, —OCH$_3$).

Methyl-4'-[(3-fluorophenylamino)methyl]biphenyl-4-carboxlyatel: $^1$H-NMR (DMSO-$d_6$, 500 MHz) δ 8.16 (2H, d, aromatic-H), 7.92 (2H, d, aromatic-H), 7.65 (2H, d, aromatic-H), 7.61 (1H, m, aromatic-H), 7.47 (2H, d, aromatic-H), 7.04 (1H, m, aromatic-H), 6.64 (1H, m, —NH), 6.43 (1H, m, aromatic-H), 6.32 (1H, m, aromatic-H), 4.32 (2H, d, —CH$_2$), 3.88 (3H, s, —OCH$_3$).

1-4 Preparation of methyl-4'-[(N-phenylpentanamido)methyl]biphenyl-2-carboxylate

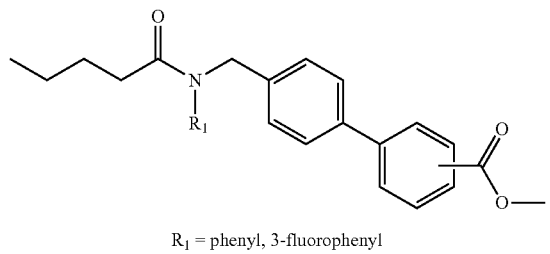

R$_1$ = phenyl, 3-fluorophenyl

Triethylamine (0.438 ml, 3.15 mmol) was added to a dichloromethane (5 mL) suspension in which methyl-4'-[(phenylamino)methyl]biphenyl-2-carboxylate (0.5 g, 1.57 mmol) obtained in Example 1-3 was dissolved. The mixture was cooled in ice, and then valeryl chloride (0.493 ml, 4.72 mmol) was slowly added for 10 minutes. After removing the ice, the mixture was stirred at room temperature for 4 hours. Then, the mixture was diluted with dichloromethane and washed with brine and water. Then, the organic solvent layer was collected, dehydrated with anhydrous MgSO$_4$, and filtered, and then the resulting organic solvent layer was concentrated by evaporation. The concentrate was purified by silica gel column chromatography (n-Hexane:EtOAc=1:4), yielding methyl-4'-[(N-phenylpentanamido)methyl]biphenyl-2-carboxylate as a colorless oil phase (1.58 g, 92% yield).

Moreover, methyl-4'-[(N-phenylpentanamido)methyl]biphenyl-3-carboxylate or methyl-4'-[(N-phenylpentanamido)methyl]biphenyl-4-carboxylate were obtained by the above method using methyl-4'-formylbiphenyl-3-carboxylate or methyl-4'-formylbiphenyl-4-carboxylate prepared in Example 1-3 using isomers different from methyl-4'-formylbiphenyl-2-carboxylate.

The obtained compounds were characterized by $^1$H-NMR, and the results are as follows:

Methyl-4'-[(N-phenylpentanamido)methyl]biphenyl-2-carboxylate: $^1$H-NMR (MeOD, 500 MHz) δ 8.15 (1H, m, aromatic-H), 7.94 (2H, m, aromatic-H), 7.60 (3H, m, aromatic-H), 7.39 (2H, m, aromatic-H), 7.31 (3H, m, aromatic-H), 7.20 (2H, m, aromatic-H), 4.91 (2H, s, —CH$_2$), 3.88 (3H, s, —OCH$_3$), 2.07 (2H, m, —CH$_2$). 1.48 (2H, m, —CH$_2$), 1.18 (2H, m, —CH$_2$), 0.76 (3H, t, —CH$_3$).

Methyl-4'-[(N-phenylpentanamido)methyl]biphenyl-3-carboxylate: $^1$H-NMR (DMSO-$d_6$, 500 MHz) δ 8.14 (1H, m, aromatic-H), 7.96 (2H, m, aromatic-H), 7.60 (3H, m, aromatic-H), 7.36 (2H, m, aromatic-H), 7.31 (3H, m, aromatic-H), 7.20 (2H, m, aromatic-H), 4.91 (2H, s, —CH$_2$), 3.88 (3H, s, —OCH$_3$), 2.07 (2H, m, —CH$_2$). 1.48 (2H, m, —CH$_2$), 1.18 (2H, m, —CH$_2$), 0.76 (3H, t, —CH$_3$).

Methyl-4'-[(N-phenylpentanamido)methyl]biphenyl-4-carboxylate: $^1$H-NMR (MeOD, 500 MHz) δ 8.06 (2H, d, aromatic-H), 7.72 (2H, d, aromatic-H), 7.60 (2H, d, aromatic-H), 7.39 (3H, m, aromatic-H), 7.31 (2H, d, aromatic-H), 7.10 (2H, d, aromatic-H), 4.91 (2H, s, —CH$_2$), 3.88 (3H, s, —OCH$_3$), 2.07 (2H, m, —CH$_2$). 1.48 (2H, m, —CH$_2$), 1.18 (2H, m, —CH$_2$), 0.76 (3H, t, —CH$_3$).

Moreover, methyl-4'-[(N-(3-fluorophenyl)pentanamido)methyl]biphenyl-2-carboxlyate, methyl-4'-[(N-(3-fluorophenyl)pentanamido)methyl]biphenyl-3-carboxlyate, or methyl-4'-[(N-(3-fluorophenyl)pentanamido)methyl]biphenyl-4-carboxlyate was obtained by the above method using methyl-4'-[(3-fluorophenylamino)methyl]biphenyl-2-carboxlyate, methyl-4'-[(3-fluorophenylamino)methyl]biphenyl-3-carboxlyate, or methyl-4'-[(3-fluorophenylamino)methyl]biphenyl-4-carboxlyate prepared in Example 1-3 using 3-fluoroaniline instead of aniline.

The obtained compounds were characterized by $^1$H-NMR, and the results are as follows:

Methyl-4'-[(N-(3-fluorophenyl)pentanamido)methyl]biphenyl-2-carboxlyate: $^1$H-NMR (DMSO-$d_6$, 500 MHz) δ 8.20 (1H, m, aromatic-H), 7.94 (1H, m, aromatic-H), 7.83 (1H, d, aromatic-H), 7.56 (2H, m, aromatic-H), 7.53 (1H, m, aromatic-H), 7.37 (1H, m, aromatic-H), 7.30 (2H, d, aromatic-H), 7.10 (1H, m, aromatic-H), 6.91 (2H, m, aromatic-H), 4.95 (2H, s, —CH$_2$), 3.88 (3H, s, —OCH$_3$,), 2.14 (2H, m, —CH$_2$). 1.49 (2H, m, —CH$_2$), 1.20 (2H, m, —CH$_2$), 0.78 (3H, t, —CH$_3$).

Methyl-4'-[(N-(3-fluorophenyl)pentanamido)methyl]biphenyl-3-carboxlyate: $^1$H-NMR (DMSO-$d_6$, 500 MHz) δ 8.21 (1H, m, aromatic-H), 7.96 (1H, d, aromatic-H), 7.83 (1H, d, aromatic-H), 7.56 (2H, m, aromatic-H), 7.53 (1H, m, aromatic-H), 7.39 (1H, m, aromatic-H), 7.30 (2H, d, aromatic-H), 7.10 (1H, m, aromatic-H), 6.94 (2H, m, aromatic-H), 4.95 (2H, s, —CH$_2$), 3.88 (3H, s, —OCH$_3$,), 2.14 (2H, m, —CH$_2$). 1.49 (2H, m, —CH$_2$), 1.20 (2H, m, —CH$_2$), 0.78 (3H, t, —CH$_3$).

Methyl-4'-[(N-(3-fluorophenyl)pentanamido)methyl]biphenyl-4-carboxlyate: $^1$H-NMR (MeOD, 500 MHz) δ 8.21 (2H, d, aromatic-H), 7.93 (2H, d, aromatic-H), 7.83 (1H, d, aromatic-H), 7.56 (2H, d, aromatic-H), 7.53 (1H, m, aromatic-H), 7.39 (1H, m, aromatic-H), 7.30 (2H, d, aromatic-H), 6.90 (1H, m, aromatic-H), 4.95 (2H, s, —CH$_2$), 3.88 (3H, s, —OCH$_3$,), 2.14 (2H, m, —CH$_2$) 0.1.49 (2H, m, —CH$_2$), 1.20 (2H, m, —CH$_2$), 0.78 (3H, t, —CH$_3$).

1-5. Preparation of 4'-[(N-phenylpentanamido)methyl]biphenyl-2-carboxylic acid

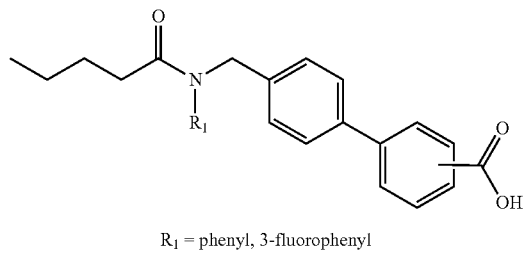

R₁ = phenyl, 3-fluorophenyl

Lithium hydroxide monohydrate (0.12 g, 2.98 mmol) was added to a THF/H₂O (1:1, 6 ml) suspension in which methyl-4'-[(N-phenylpentanamido)methyl]biphenyl-2-carboxylate (0.3 g, 0.74 mmol) obtained in Example 1-4 was dissolved, and the mixture was stirred at room temperature overnight. The mixture was neutralized with 10% HCL, diluted with ethyl acetate, and washed with brine and water. Then, the organic solvent layer was collected, dehydrated with anhydrous MgSO₄, and filtered, and then the resulting organic solvent layer was concentrated by evaporation. The concentrate was purified by silica gel column chromatography (n-Hexane:EtOAc=1:4), yielding 4'-[(N-phenylpentanamido)methyl]biphenyl-2-carboxylic acid as a white solid phase (0.26 g, 94% yield).

Moreover, 4'-[(N-phenylpentanamido)methyl]biphenyl-3-carboxylic acid or 4'-[(N-phenylpentanamido)methyl]biphenyl-4-carboxylic acid was obtained by the above method using methyl-4'-[(N-phenylpentanamido)methyl]biphenyl-3-carboxylate or methyl-4'-[(N-phenylpentanamido)methyl]biphenyl-4-carboxylate prepared in Example 1-4 using isomers different from methyl-4'-[(phenylamino)methyl]biphenyl-2-carboxylate.

The obtained compounds were characterized by ¹H-NMR, and the results are as follows:

4'-[(N-phenylpentanamido)methyl]biphenyl-2-carboxylic acid (hereinafter referred to as compound 1):

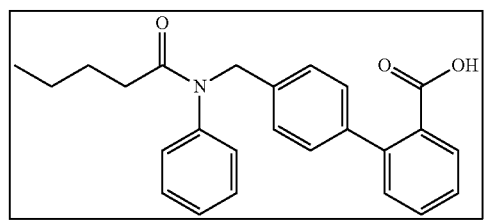 [SMILES: CCCCC(=O)N(Cc1ccc(-c2ccccc2C(=O)O)cc1)c1ccccc1]

¹H-NMR (DMSO-d₆, 500 MHz) δ 12.7 (1H, brs, —OH), 8.15 (1H, m, aromatic-H), 7.94 (2H, m, aromatic-H), 7.60 (3H, m, aromatic-H), 7.39 (2H, m, aromatic-H), 7.31 (3H, m, aromatic-H), 7.20 (2H, m, aromatic-H), 4.91 (2H, s, —CH₂), 2.07 (2H, m, —CH₂) 0.1.48 (2H, m, —CH₂), 1.18 (2H, m, —CH₂), 0.76 (3H, t, —CH₃).

4'-[(N-phenylpentanamido)methyl]biphenyl-3-carboxylic acid (hereinafter referred to as compound 2):

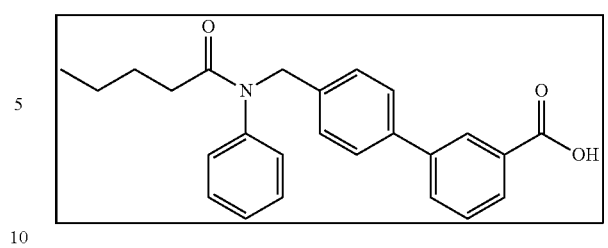

¹H-NMR (DMSO-d₆, 500 MHz) δ 13.1 (1H, brs, —OH), 8.14 (1H, m, aromatic-H), 7.92 (2H, m, aromatic-H), 7.61 (2H, m, aromatic-H), 7.57 (1H, m, aromatic-H), 7.40 (2H, m, aromatic-H), 7.30 (3H, m, aromatic-H), 7.19 (2H, d, aromatic-H), 4.91 (2H, s, —CH₂), 2.07 (2H, m, —CH₂) 0.1.48 (2H, m, —CH₂), 1.18 (2H, m, —CH₂), 0.76 (3H, t, —CH₃).

4'-[(N-phenylpentanamido)methyl]biphenyl-4-carboxylic acid (hereinafter referred to as compound 3):

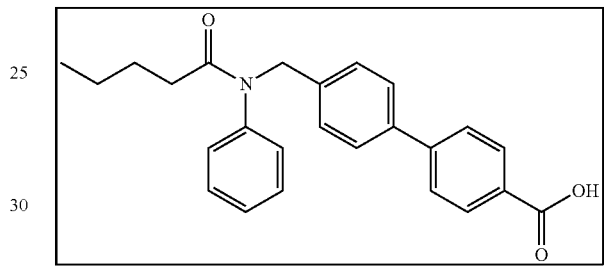

¹H-NMR (DMSO-d₆, 500 MHz) δ 13.0 (1H, brs, —OH), 8.00 (2H, d, aromatic-H), 7.77 (2H, d, aromatic-H). 7.66 (2H, d, aromatic-H), 7.39 (2H, m, aromatic-H), 7.31 (3H, m, aromatic-H), 7.20 (2H, d, aromatic-H), 4.91 (2H, s, —CH₂), 2.08 (2H, m, —CH₂) CH₂), 1.18 (2H, m, —CH₂), 0.76 (3H, t, —CH₃).

Moreover, 4'-[(N-(3-fluorophenyl)pentanamido)methyl]biphenyl-2-carboxylic acid, 4'-[(N-(3-fluorophenyl)pentanamido)methyl]biphenyl-3-carboxylic acid, or 4'-[(N-(3-fluorophenyl)pentanamido)methyl]biphenyl-4-carboxylic acid was obtained by the same method as Examples 1-4 and 1-5 using methyl-4'-[(N-(3-fluorophenyl)pentanamido)methyl]biphenyl-2-carboxlyate, methyl-4'-[(N-(3-fluorophenyl)pentanamido)methyl]biphenyl-3-carboxlyate, or methyl-4'-[(N-(3-fluorophenyl)pentanamido)methyl]biphenyl-4-carboxlyate prepared in Example 1-3 using 3-fluoroaniline instead of aniline.

The obtained compounds were characterized by ¹H-NMR, and the results are as follows:

4'-[(N-(3-fluorophenyl)pentanamido)methyl]biphenyl-2-carboxylic acid (hereinafter referred to as compound 7):

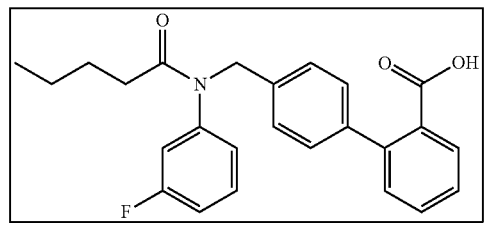 [SMILES: CCCCC(=O)N(Cc1ccc(-c2ccccc2C(=O)O)cc1)c1cccc(F)c1]

¹H-NMR (DMSO-d₆, 500 MHz) δ 12.8 (1H, brs, —OH), 7.7 (1H, m, aromatic-H), 7.55 (1H, m, aromatic-H), 7.45 (2H, m, aromatic-H), 7.35 (2H, m, aromatic-H), 7.25 (2H, m, aromatic-H), 7.20 (3H, m, aromatic-H) 7.05 (1H, m, aromatic-H), 4.93 (2H, s, —CH₂), 2.14 (2H, m, —CH₂). 1.49 (2H, m, —CH₂), 1.20 (2H, m, —CH₂), 0.78 (3H, t, —CH₃).

4'-[(N-(3-fluorophenyl)pentanamido)methyl]biphenyl-3-carboxylic acid (hereinafter referred to as compound 8):

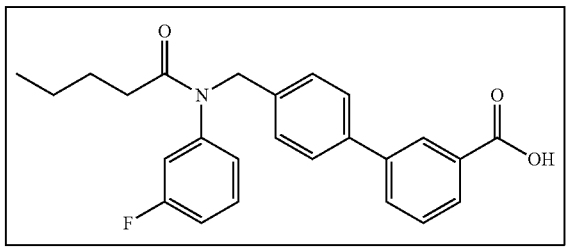 [SMILES: CCCCC(=O)N(Cc1ccc(-c2cccc(C(=O)O)c2)cc1)c1cccc(F)c1]

¹H-NMR (DMSO-d₆, 500 MHz) s 13.1 (1H, brs, —OH), 8.12 (1H, d, aromatic-H), 7.85 (2H, d, aromatic-H), 7.66 (2H, d, aromatic-H), 7.56 (2H, m, aromatic-H), 7.20 (2H, m, aromatic-H), 7.20 (2H, m, aromatic-H) 7.05 (1H, m, aromatic-H), 4.91 (2H, s, —CH₂), 2.08 (2H, m, —CH₂). 1.48 (2H, m, —CH₂), 1.18 (2H, m, —CH₂), 0.76 (3H, t, —CH₃CH₃).

4'-[(N-(3-fluorophenyl)pentanamido)methyl]biphenyl-4-carboxylic acid (hereinafter referred to as compound 9):

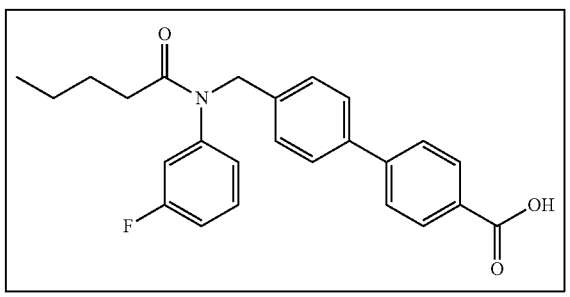 [SMILES: CCCCC(=O)N(Cc1ccc(-c2ccc(C(=O)O)cc2)cc1)c1cccc(F)c1]

¹H-NMR (DMSO-d₆, 500 MHz) δ 13.2 (1H, brs, —OH), 8.14 (1H, m, aromatic-H), 7.90 (2H, m, aromatic-H), 7.62 (2H, d, aromatic-H), 7.57 (1H, m, aromatic-H), 7.41 (1H, m, aromatic-H), 7.30 (2H, d, aromatic-H), 7.20 (2H, m, aromatic-H) 7.05 (1H, m, aromatic-H), 4.93 (2H, s, —CH₂), 2.14 (2H, m, —CH₂). 1.49 (2H, m, —CH₂), 1.20 (2H, m, —CH₂), 0.78 (3H, t, —CH₃).

Moreover, 4'-[(N-(3-fluorophenyl)hexanamido)methyl]biphenyl-4-carboxylic acid was obtained using methyl-4'-[(phenylamino)methyl]biphenyl-4-carboxylate prepared in Example 1-3 by the above method using caproyl chloride instead of valeryl chloride used in Example 1-4.

The obtained compounds were characterized by ¹H-NMR, and the results are as follows:

4'-[(N-(3-fluorophenyl)hexanamido)methyl]biphenyl-4-carboxylic acid (hereinafter referred to as compound 10):

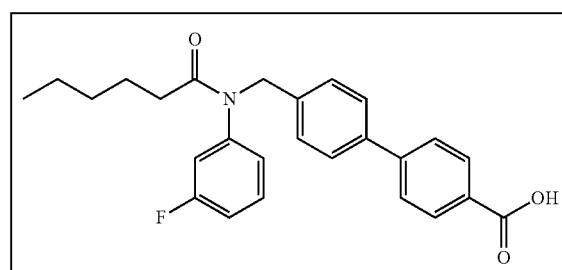

¹H-NMR (CDCl₃, 500 MHz) d 8.15 (2H, d, aromatic-H), 7.67 (2H, d, aromatic-H), 7.55 (2H, d, aromatic-H), 7.30 (2H, d, aromatic-H), 7.04 (1H, m, aromatic-H), 6.82 (1H, d, aromatic-H) 6.77 (1H, d, aromatic-H), 4.92 (2H, s, —CH₂), 2.12 (2H, t, —CH₂). 1.62 (2H, m, —CH₂), 1.22 (4H, m, —CH₂), 0.87 (3H, t, —CH₃).

1-6. Preparation of N-[(2'-(4-methylpiperazine-1-carbonyl)biphenyl-4-yl)methyl]-N-phenylpentanamide

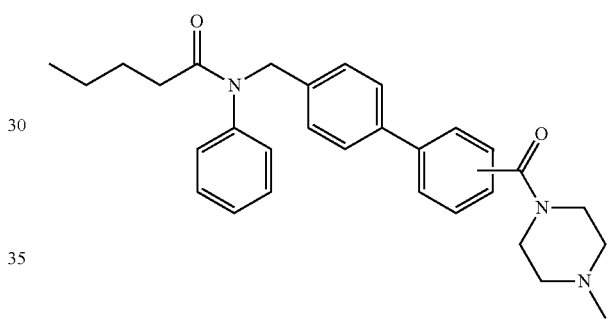

DIPEA (N,N-Diisopropylethylamine (0.13 ml, 0.74 mmol) was added to a DMF (2 mL) suspension in which 4'-[(N-phenylpentanamido)methyl]biphenyl-2-carboxylic acid (0.1 g, 0.25 mmol) prepared in Example 1-5, 1-methylpiperazine (0.03 ml, 0.30 mmol), and HATU (2-(1H-7-azabenzotriazol-1-yl)-1,1,3,3-tetramethyluronium hexafluorophosphate) (0.11 g, 0.30 mmol) were dissolved, and the mixture was stirred at room temperature overnight. The mixture was cooled in ice, and then valeryl chloride (0.493 ml, 4.72 mmol) was slowly added for 10 minutes. After removing the ice, the mixture was stirred at room temperature for 4 hours. Then, the mixture was diluted with dichloromethane and washed with brine and water. Then, the organic solvent layer was collected, dehydrated with anhydrous MgSO₄, and filtered, and then the resulting organic solvent layer was concentrated by evaporation. The concentrate was purified by silica gel column chromatography (CH₂Cl₂:MeOH=4.5:0.5), yielding N-[(2'-(4-methylpiperazine-1-carbonyl)biphenyl-4-yl)methyl]-N-phenylpentanamide as a pale yellow oil phase (0.11 g, 93% yield).

Moreover, N-[(3'-(4-methylpiperazine-1-carbonyl)biphenyl-4-yl)methyl]-N-phenylpentanamide or N-[(4'-(4-methylpiperazine-1-carbonyl)biphenyl-4-yl)methyl]-N-phenylpentanamide was obtained by the above method using 4'-[(N-phenylpentanamido)methyl]biphenyl-3-carboxylic acid or 4'-[(N-phenylpentanamido)methyl]biphenyl-4-carboxylic acid prepared in Example 1-5 using isomers different from methyl-4'-[(N-phenylpentanamido)methyl]biphenyl-2-carboxylic acid.

The obtained compounds were characterized by ¹H-NMR, and the results are as follows:

N-[(2'-(4-methylpiperazine-1-carbonyl)biphenyl-4-yl)methyl]-N-phenylpentanamide (hereinafter referred to as compound 4):

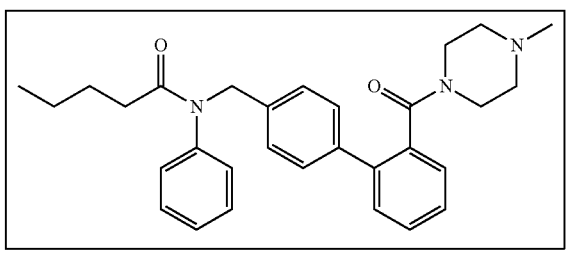

¹H-NMR (DMSO-d₆, 500 MHz) δ 7.71 (1H, m, aromatic-H), 7.61 (3H, m, aromatic-H), 7.51 (1H, m, aromatic-H), 7.39 (2H, m, aromatic-H), 7.34 (2H, m, aromatic-H), 7.27 (2H, m, aromatic-H), 7.19 (2H, m, aromatic-H), 4.90 (2H, s, —CH₂), 3.6 (4H, d, -piperazine), 2.36 (4H, d, -piperazine), 2.19 (3H, s, piperazine-CH₃) 0.2.07 (2H, m, —CH₂) 0.1.48 (2H, m, —CH₂), 1.18 (2H, m, —CH₂), 0.76 (3H, t, —CH₃).

N-[(3'-(4-methylpiperazine-1-carbonyl)biphenyl-4-yl)methyl]-N-phenylpentanamide (hereinafter referred to as compound 5):

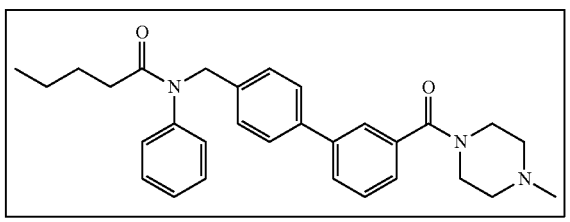 [SMILES: CCCCC(=O)N(Cc1ccc(-c2cccc(C(=O)N3CCN(C)CC3)c2)cc1)c1ccccc1]

¹H-NMR (DMSO-d₆, 500 MHz) δ 7.71 (1H, m, aromatic-H), 7.61 (3H, m, aromatic-H), 7.51 (1H, m, aromatic-H), 7.42 (2H, m, aromatic-H), 7.30 (2H, m, aromatic-H), 7.25 (2H, m, aromatic-H), 7.19 (2H, m, aromatic-H), 4.90 (2H, s, —CH₂), 3.16 (4H, d, -piperazine), 2.38 (4H, d, -piperazine), 2.18 (3H, s, piperazine-CH₃). 2.07 (2H, m, —CH₂) 0.1.48 (2H, m, —CH₂), 1.18 (2H, m, —CH₂), 0.76 (3H, t, —CH₃).

N-[(4'-(4-methylpiperazine-1-carbonyl)biphenyl-4-yl)methyl]-N-phenylpentanamide (hereinafter referred to as compound 6):

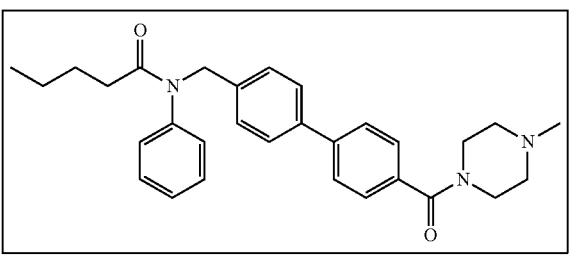 [SMILES: CCCCC(=O)N(Cc1ccc(-c2ccc(C(=O)N3CCN(C)CC3)cc2)cc1)c1ccccc1]

¹H-NMR (DMSO-d₆, 500 MHz) δ 7.95 (1H, m, aromatic-H), 7.70 (2H, d, aromatic-H), 7.62 (2H, d, aromatic-H), 7.44 (2H, d, aromatic-H), 7.36 (2H, m, aromatic-H), 7.27 (2H, m, aromatic-H), 7.19 (2H, d, aromatic-H), 4.90 (2H, s, —CH₂), 3.01 (4H, d, -piperazine), 2.5 (3H, s, piperazine-CH₃). 2.36 (4H, d, -piperazine), 2.07 (2H, m, —CH₂). 1.48 (2H, m, —CH₂), 1.18 (2H, m, —CH₂), 0.76 (3H, t, —CH₃).

Moreover, N-(3-fluorophenyl)-N-[(4'-(morpholine-4-carbonyl)biphenyl-4-yl)methyl]pentanamide was obtained using 4'-[(N-(3-fluorophenyl)pentanamido)methyl]biphenyl-4-carboxylic acid prepared in Example 1-5 and using morpholine instead of 1-methylpiperazine.

The obtained compound was characterized by ¹H-NMR, and the results are as follows:

N-(3-fluorophenyl)-N-[(4'-(morpholine-4-carbonyl)biphenyl-4-yl)methyl]pentanamide (hereinafter referred to as compound 11):

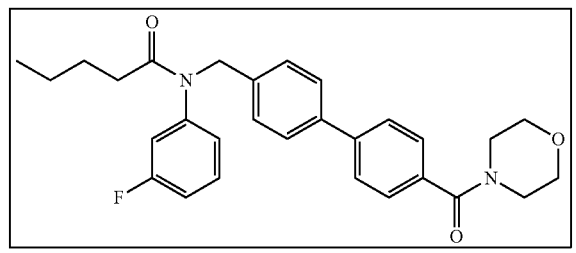 [SMILES: CCCCC(=O)N(Cc1ccc(-c2ccc(C(=O)N3CCOCC3)cc2)cc1)c1cccc(F)c1]

¹H-NMR (CDCl₃, 500 MHz) δ 7.61 (1H, d, aromatic-H), 7.47 (4H, m, aromatic-H), 7.32 (1H, t, aromatic-H), 7.28 (2H, d, aromatic-H), 7.03 (2H, m, aromatic-H), 6.82 (2H, d, aromatic-H), 6.76 (2H, d, aromatic-H), 4.91 (2H, s, —CH₂), 3.71 (8H, bs, -morpholine), 2.11 (2H, d, —CH₂). 1.62 (2H, m, —CH₂), 1.25 (2H, m, —CH₂), 0.84 (3H, t, —CH₃).

Moreover, N-(3-fluorophenyl)-N-[(4'-(4-methylpiperazine-1-carbonyl) biphenyl-4-yl)methyl]hexanamide was obtained by the above method using 4'-[(N-(3-fluorophenyl)hexanamido)methyl]biphenyl-4-carboxylic acid prepared in Example 1-5.

The obtained compound was characterized by ¹H-NMR, and the results are as follows:

N-(3-fluorophenyl)-N-[(4'-(4-methylpiperazine-1-carbonyl)biphenyl-4-yl)methyl]hexanamide (hereinafter referred to as compound 12):

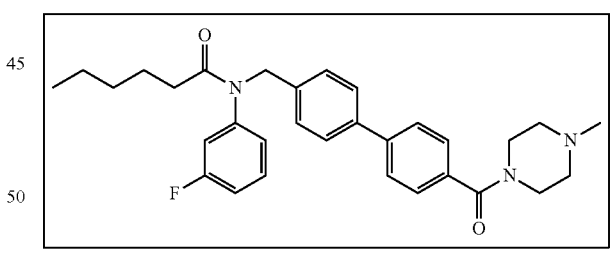

¹H-NMR (CDCl₃, 400 MHz) d 7.60 (2H, d, aromatic-H), 7.48 (4H, m, aromatic-H), 7.32 (3H, m, aromatic-H), 7.03 (1H, m, aromatic-H), 6.82 (1H, d, aromatic-H), 6.76 (1H, d, aromatic-H), 4.91 (2H, s, —CH₂), 3.64 (4H, dd, -piperazine), 2.48 (4H, dd, -piperazine). 2.33 (3H, s, —CH₃), 2.12 (2H, t, —CH₂), 1.64 (2H, m, —CH₂), 1.23 (4H, m, —CH₂), 0.84 (3H, t, —CH₃).

Experimental Example 1

Analysis of Phagocytosis

The following experiment was performed to analyze the phagocytosis of the novel biphenyl compounds obtained in Example 1. $5 \times 10^4$ RAW264.7 cells, mouse macrophages, were plated in a 24 well plate and pre-incubated in a 5% $CO_2$ incubator at 37° C. for 18 hours. The medium was replaced with a new medium before treatment with the compounds, and the cells were treated with the compounds obtained in Example 1 at a concentration of 10 μM and incubated at 37° C. for 15 minutes. Then, the cells were treated with FITC-zymosan A (the ratio of macrophages to particle was 1:10) and incubated at 4° C. for 30 minutes such that the particles were attached to the cells. Then, the cells were washed with a serum-free culture medium to remove unattached particles and incubated at 37° C. for 30 minutes. The cells were observed under a microscope at a magnification of ×200. The phagocytosis of macrophages was determined when two or more particles were observed in macrophages, and the phagocytic activity was calculated by the following equation:

Phagocytic activity (%)=(the number of cells causing phagocytosis/the number of cells observed in each field of view at a magnification of ×200) *100

Figure 2:
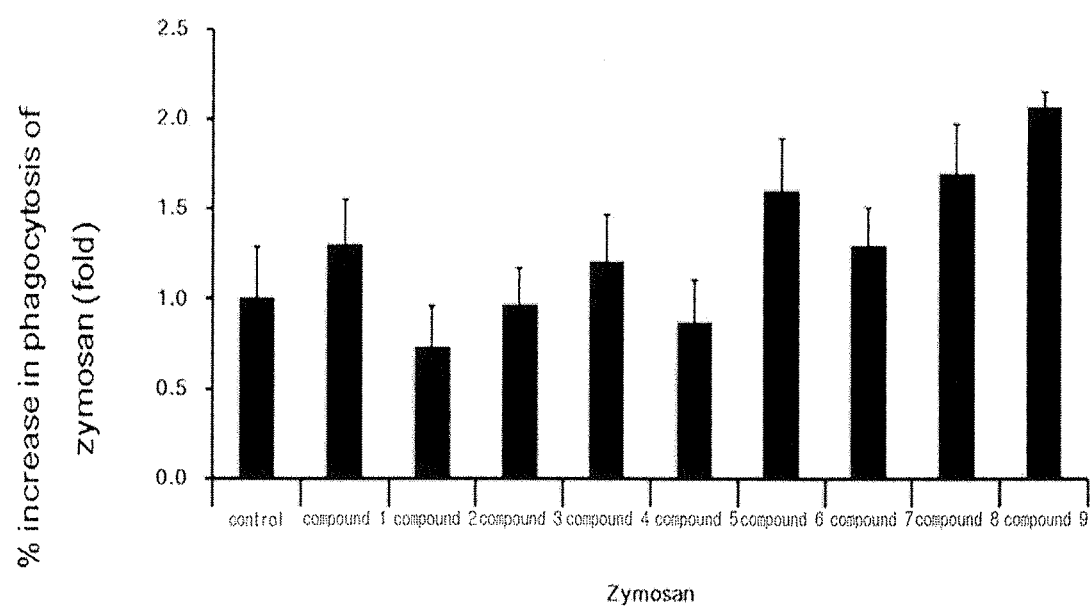
FIG. 2 is a plot showing the promotion of phagocytosis of macrophages by biphenyl derivatives of the present invention.
Figure 3:
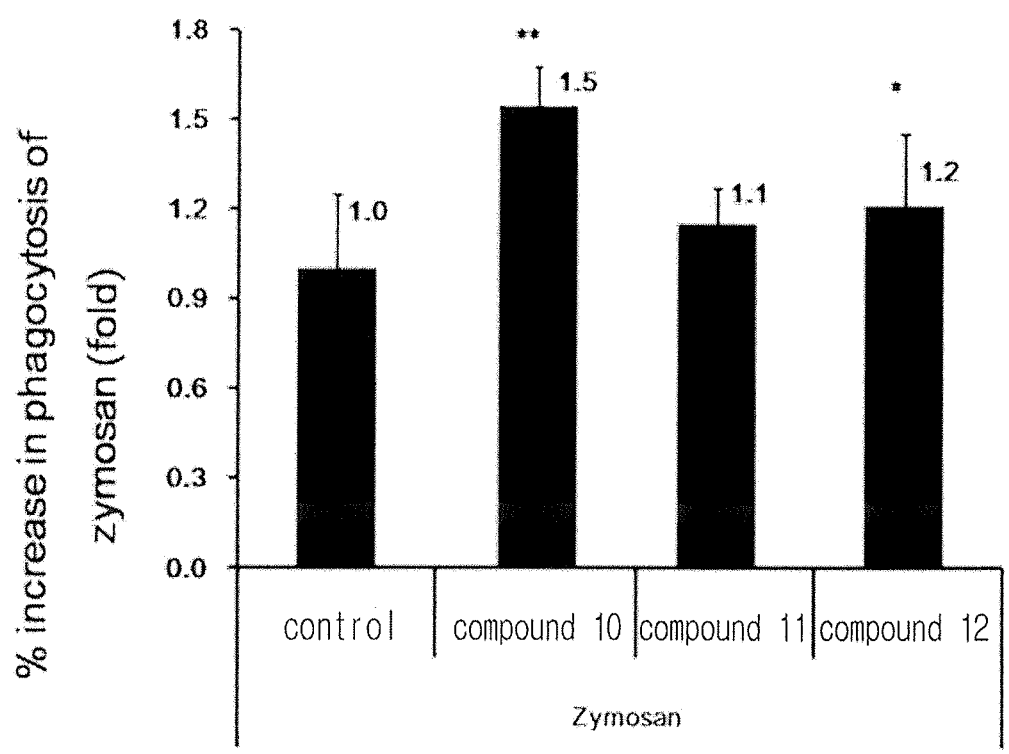
FIG. 3 is a plot showing the promotion of phagocytosis of macrophages by biphenyl derivatives of the present invention.

The results are shown in FIGS. 1 to 3.

As shown in FIGS. 1 to 3, it was found that the biphenyl derivatives of the present invention promoted the phagocytosis of macrophages.

Experimental Example 2

Analysis of Chemotaxis

The following experiment was performed using a ChemoTx 96-well chamber (Neuroprobe, Inc., Gaithersburg, Md.) to analyze the chemotaxis of the novel biphenyl compounds obtained in Example 1. HT1080 cells were suspended in an RPMI medium at a concentration of $2 \times 10^5$ cells/ml, and 30 ul of the suspension was added to the upper chamber. WKYMVm peptide was added to the lower chamber separated by a membrane. The cells were treated with the compounds obtained in Example 1, incubated at 37° C. for 3 hours, and stained using a Diff-Quick staining kit (Kobe, Japan). The cells were observed under a microscope and counted. The results are shown in FIG. 4.

Figure 4:
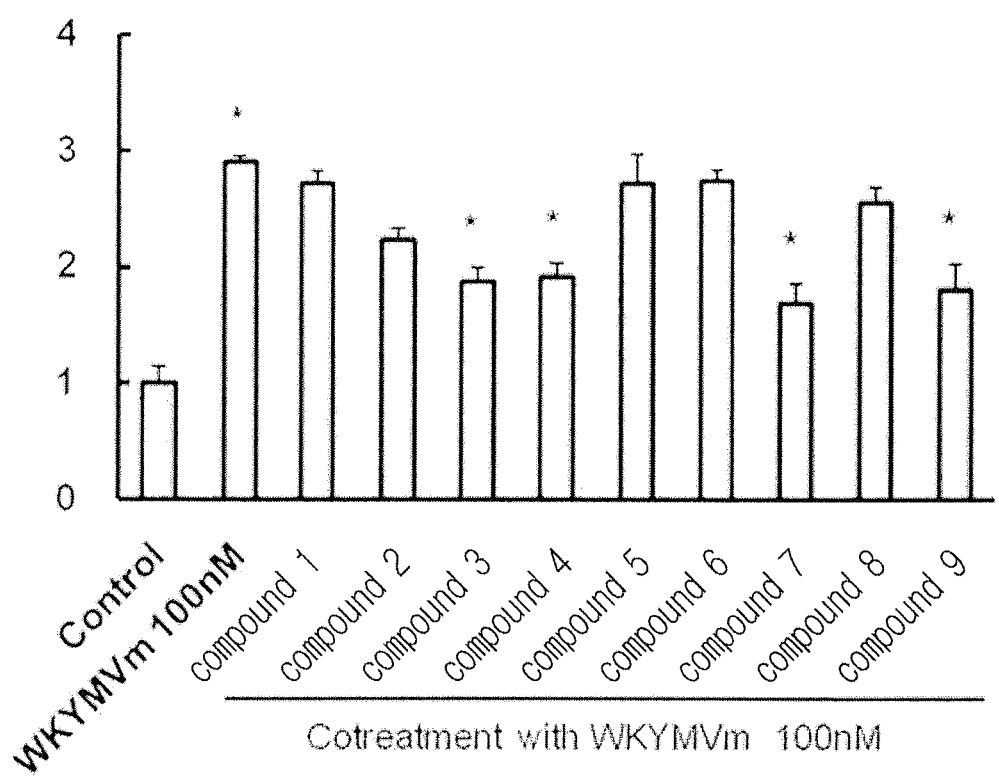
FIG. 4 is a plot showing the inhibition of cell migration by biphenyl derivatives of the present invention.

As shown in FIG. 4, it was found that the biphenyl derivatives of the present invention inhibited the chemotaxis of macrophages.

Experimental Example 3

Analysis of Anti-Inflammatory Activity

The following experiment was performed using tetradecanoyl phorbol acetate (TPA)-induced ear edema (inflammation) mouse models to analyze the anti-inflammatory activity of the novel biphenyl compounds obtained in Example 1. The TPA-induced ear edema mouse model has been widely used to investigate the mechanism of the inflammatory response and the effects of inhibitory substances (Agents and Actions. 1989. 26; 335-341). More specifically, 6-week-old ICR male mice were prepared, and each 20 μl of a TPA solution dissolved in acetone at a concentration of 125 μg/ml was applied to the left ears of mice. After 1 hour of the TPA application, each 20 μl of the solvent or compound 6 (0.3% and 1%) prepared in Example 1 and dissolved in the solvent was applied to the left ears of mice and reapplied after 6 hours of the TPA application. Indomethacin, an anti-inflammatory agent, was applied to the positive control group. Each predetermined area of the left ears of mice was harvested after 24 hours of the TPA application. The weight of each of the left ears of mice was measured, and H&E staining and immunohistochemical staining were performed on ear tissues. The results are shown in FIGS. 5 to 8.

Figure 5:
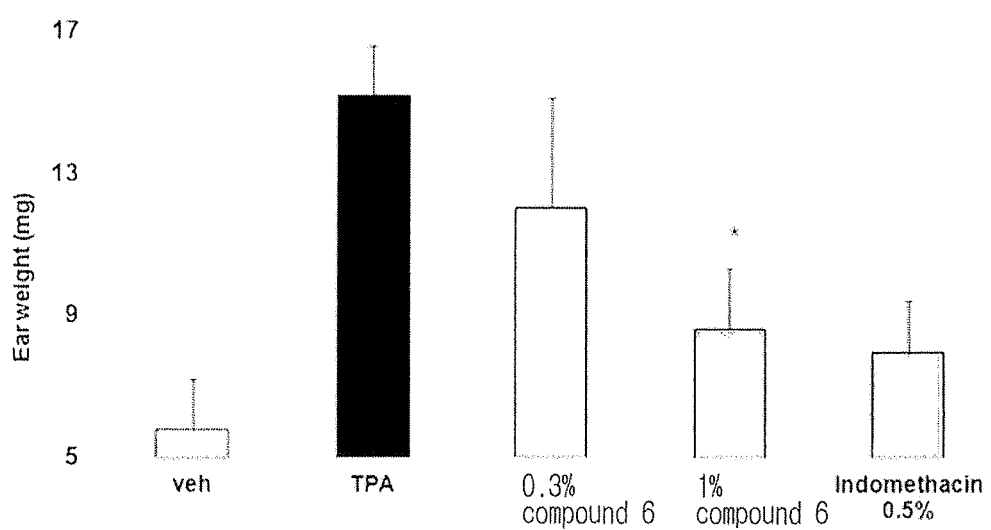
FIG. 5 is a plot showing the anti-inflammatory and anti-edema activities of a biphenyl derivative of the present invention.

As shown in FIG. 5, it was found that the inflammation and edema induced by TPA were inhibited in the mice treated with N-[(2'-(4-methylpiperazine-1-carbonyl)biphenyl-4-yl)methyl]-N-phenylpentanamide, one of the biphenyl'derivatives of the present invention.

Figure 6:
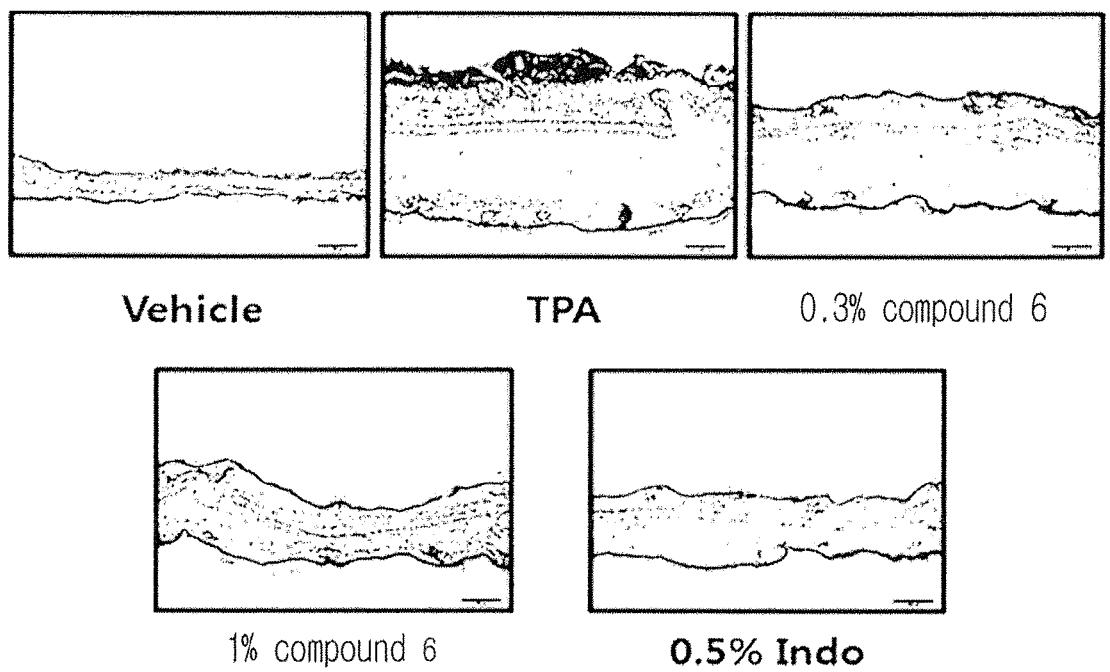
FIG. 6 is a montage of photomicrographs showing the anti-inflammatory and anti-edema activities of a biphenyl derivative of the present invention.

Moreover, as shown in FIG. 6, it was found that the ear tissues thickened by the edema induced by TPA were recovered to normal level in the mice treated with N-[(2'-(4-methylpiperazine-1-carbonyl)biphenyl-4-yl)methyl]-N-phenylpentanamide, one of the biphenyl derivatives of the present invention.

Figure 7:
FIG. 7 is a montage of photomicrographs showing the effect of a biphenyl derivative of the present invention on the expression of inflammation-related protein p65.
Figure 7:
Figure 7:
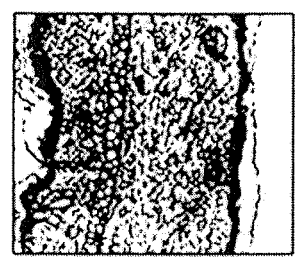
Figure 7:
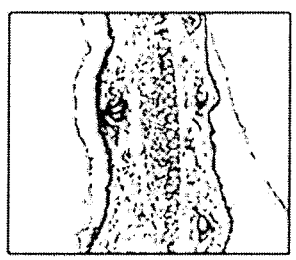
Figure 7:
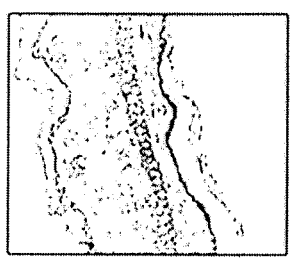
Figure 8:
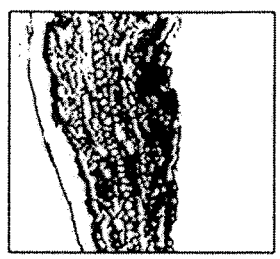
FIG. 8 is a montage of photomicrographs showing the effect of a biphenyl derivative of the present invention on the expression of anti-inflammatory protein IkB (inhibitory kappa B).
Figure 8:
Figure 8:
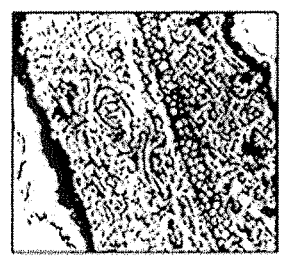
Figure 8:
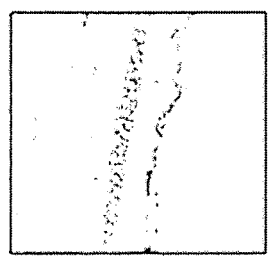
Figure 8:
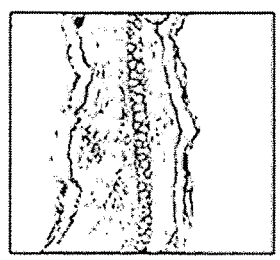

Furthermore, as shown in FIGS. 7 and 8, it was found that the expression of inflammation-related protein p65 decreased and the expression of anti-inflammatory protein IkB (inhibitory kappa B) increased in the mice treated with N-[(2'-(4-methylpiperazine-1-carbonyl)biphenyl-4-yl) methyl]-N-phenylpentanamide, one of the biphenyl derivatives of the present invention.

Next, Preparation Examples of the pharmaceutical composition of the present invention will be described, but these Preparation Examples are not intended to limit the present invention, but are intended to more fully describe the present invention.

Preparation Examples

Preparation of Pharmaceutical Compositions

1. Preparation of Powders

| | |
|---|---|
| Biphenyl derivative or pharmaceutically acceptable salt thereof of the present invention: | 20 mg |
| Lactose: | 100 mg |
| Talc: | 10 mg |

The above ingredients are mixed and packed in airtight bags to prepare powders.

2. Preparation of Tablets

| | |
|---|---|
| Biphenyl derivative or pharmaceutically acceptable salt thereof of the present invention: | 10 mg |
| Corn starch: | 100 mg |
| Lactose: | 100 mg |
| Magnesium stearate: | 2 mg |

The above ingredients are mixed and compressed into tablets according to a conventional method for preparing tables.

3. Preparation of Capsules

| | |
|---|---|
| Biphenyl derivative or pharmaceutically acceptable salt thereof of the present invention: | 10 mg |
| Crystalline cellulose: | 3 mg |
| Lactose: | 14.8 mg |
| Magnesium stearate: | 0.2 mg |

The above ingredients are mixed and filled in gelatin capsules to prepare according to a conventional method for preparing capsules.

4. Preparation of Infections

| | |
|---|---|
| Biphenyl derivative or pharmaceutically acceptable salt thereof of the present invention: | 10 mg |
| Mannitol: | 180 mg |
| Sterile distilled water for injection: | 2,974 mg |
| Na$_2$HPO$_4$·2H$_2$O: | 26 mg |

Injections are prepared with the above ingredients per ampoule (2 ml) according to a conventional method for preparing injections.

5. Preparation of Liquid Formulations

| | |
|---|---|
| Biphenyl derivative or pharmaceutically acceptable salt thereof of the present invention: | 20 mg |
| Isomerized sugar: | 10 g |
| Mannitol: | 5 mg |
| Purified water: | Suitable amount |

Liquid formulations are prepared by dissolving the above ingredients in purified water, adding a suitable amount of lemon flavor, mixing the above ingredients, adding purified water to the mixture to adjust the volume to 100 ml water, loading the liquid into brown bottles, and sterilizing according to a conventional method for preparing liquid formulations.

INDUSTRIAL APPLICABILITY

The novel biphenyl derivatives or pharmaceutically acceptable salts thereof according to the present invention promote the phagocytosis of macrophages and inhibit the chemotaxis to exhibit excellent inflammation terminating and anti-inflammatory effects and thus can be effectively used as therapeutic agents for inflammatory diseases or autoimmune diseases.

The invention claimed is:

1. A biphenyl compound or a pharmaceutically acceptable salt thereof, wherein the biphenyl compound is selected from the group consisting of the following compounds 4) N-[(2'-(4-methylpiperazine-1-carbonyl)biphenyl-4-yl)methyl]-N-phenylpentanamide;
5) N-[(3'-(4-methylpiperazine-1-carbonyl)biphenyl-4-yl)methyl]-N-phenylpentanamide;
6) N-[(4'-(4-methylpiperazine-1-carbonyl)biphenyl-4-yl)methyl]-N-phenylpentanamide;
7) 4'-[(N-(3-fluorophenyl)pentanamido)methyl]biphenyl-2-carboxylic acid;
8) 4'-[(N-(3-fluorophenyl)pentanamido)methyl]biphenyl-3-carboxylic acid;
9) 4'-[(N-(3-fluorophenyl)pentanamido)methyl]biphenyl-4-carboxylic acid;
10) 4'-[(N-(3-fluorophenyl)hexanamido)methyl]biphenyl-4-carboxylic acid;
11) N-(3-fluorophenyl)-N-[(4'-(morpholine-4-carbonyl)biphenyl-4-yl)methyl]pentanamide; and
12) N-(3-fluorophenyl)-N-[(4'-(4-methylpiperazine-1-carbonyl)biphenyl-4-yl)methyl]hexanamide.

2. A pharmaceutical composition for treating inflammatory diseases or autoimmune diseases, the pharmaceutical composition comprising
the biphenyl compound or a pharmaceutically acceptable salt thereof of claim 1 as an active ingredient and a pharmaceutically acceptable carrier, excipient, or diluent, wherein the inflammatory diseases or autoimmune diseases are selected from the group consisting of irritable colitis, rheumatoid arthritis, multiple sclerosis, acute inflammatory diseases, chronic inflammatory diseases, atheriosclerosis, chronic obstructive pulmonary disease, sepsis and asthma.

3. The pharmaceutical composition of claim 2, wherein the inflammatory diseases or autoimmune diseases are caused by abnormal termination of inflammation.

4. A method for treating an inflammatory disease or autoimmune disease, the method comprising administering an effective amount of the pharmaceutical compositions of claim 2 to a patient, wherein the inflammatory disease is selected from the group consisting of irritable colitis, rheumatoid arthritis, multiple sclerosis, acute inflammatory diseases, chronic inflammatory diseases, atheriosclerosis, chronic obstructive pulmonary disease, sepsis and asthma.

* * * * *